United States Patent [19]

Huser et al.

[11] Patent Number: 4,600,777

[45] Date of Patent: Jul. 15, 1986

[54] METHOD OF PREPARING 1-ALKYL-7-OXODECAHYDROQUINO-LINES, AND CIS(±) AND TRAN(±)ISOMERS SO PREPARED

[75] Inventors: Diane L. Huser; John M. Schaus; Robert D. Titus; Leland O. Weigel, all of Indianapolis, Ind.

[73] Assignee: Eli Lilly and Company, Indianapolis, Ind.

[21] Appl. No.: 637,181

[22] Filed: Aug. 2, 1984

[51] Int. Cl.$^4$ ............................................. C07D 215/20
[52] U.S. Cl. ..................................................... 546/164
[58] Field of Search ................................. 546/164, 165

[56] References Cited

U.S. PATENT DOCUMENTS 4,198,415 4/1980 Kornfeld et al. ..................... 546/164

OTHER PUBLICATIONS

Johnson et al., *J. Org. Chem.*, 33, 3207 (1968).
Momose et al., *Chem. Pharm. Bull.*, 25, 1436 (1977) Momose I.
Momose et al., ibid, 1797, Momose II.
Momose et al., ibid, 26, 620 (1978) Momose III.
Pearson et al., *J. Chem. Soc. Perkin Trans.*, 1983, 619.
Huck et al, "Liebigs Ann. der Chemie", (1927), 453, pp. 163–176.

*Primary Examiner*—Richard L. Raymond
*Assistant Examiner*—D. B. Springer
*Attorney, Agent, or Firm*—Charles W. Ashbrook; Arthur R. Whale

[57] ABSTRACT

1-$C_{1-3}$ straight chain alkyl 7-oxodecahydroquinoline, chemical intermediates.

6 Claims, No Drawings

METHOD OF PREPARING 1-ALKYL-7-OXODECAHYDROQUINOLINES, AND CIS(±) AND TRAN(±)ISOMERS SO PREPARED

BACKGROUND OF THE INVENTION

4aS,8aS-1-benzoyl-7-oxodecahydroquinoline has been prepared, among other compounds by the hydroxylating action of *Sporotrichium sulfurescens* on the substrate 4aS,8aS-1-benzoyldecahydroquinoline followed by $CrO_3$ oxidation. $LiAlH_4$ reduction of the mold metabolic product gave 4aS,8aS-1-benzyl-7-hydroxydecahydroquinoline. Debenzylation with hydrogen using a palladium-on-carbon catalyst produced 4aS,8aS-7-hydroxydecahydroquinoline. The corresponding 4aR,-8aR-derivative was not found in the fermentation when the 4aS,8aS starting material was used. The above chemistry is outlined in a paper by Johnson et al., *J. Org. Chem.*, 33, 3207 (1968) where 4aS,8aS-7-oxodecahydroquinoline is compound no. 26 (named as a quinolin-7-one).

Momose and coworkers at Osaka U. have prepared a series of octahydro-7(1H)-quinolines. Paper no. I appearing in *Chem. Pharm. Bull.*, 25, 1436 (1977) discusses the results of hydrogenating 7-hydroxyquinoline over 5% $Rh/Al_2O_3$. N-benzylation via the N-benzoyl derivative gave four products, a cis-dl-mixture and a trans-dl-mixture. The individual racemates were obtained by chromatography. The preparation of trans(±)-7β-hydroxydecahydroquinoline (XVIII) from trans-(±)-7-oxodecahydroquinoline (XIa) was also outlined. Paper no. II (ibid 1797) prepares cis-(±)-7-oxodecahydroquinoline by two different procedures. Paper no. III (ibid 26, 620 (1978)] discusses the isomerization of the cis-(±) and trans-(±)-7-oxodecahydroquinolines.

Pearson et al *J.C.S., Perkin Transactions*, I 619 (1983) also discloses the preparation of cis-(±)-7-oxodecahydroquinolines carrying a substituent at 4a.

It is an object of this invention to provide an improved synthetic route to trans-(±)-7-oxdecahydroquinoline which route is free from the isomer problems which beset the prior art synthetic procedures.

DESCRIPTION OF THE INVENTION

The novel synthetic process of this invention, graphically set forth in Reaction Scheme I, involves, as a first step, the Birch reduction of a 4-(3-$C_{1-3}$ straight chain alkylamino)propylanisole (I) to yield a 1-methoxy-4-(3-$C_{1-3}$ straight-chain alkylamino)propyl-1,4-cyclohexadiene (II). Mild acidic hydrolysis of the enol ether yields a 4-(3-$C_{1-3}$ straight-chain alkylamino)propyl-3-cyclohexene-1-one (III) which, under more rigorous acid treatment followed by treatment with base, cyclizes to yield a cis-(±)-1-$C_{1-3}$ straight-chain alkyl-7-oxodecahydroquinoline (IV). Treatment of the cis(±)-racemate with base in a mutual inert polar solvent, conveniently sodium methylate in methanol, isomerizes the cis (±)-racemate to the trans-(±)-1-$C_{1-3}$ straight-chain alkyl-7-oxodecahydroquinoline (IV).

Alternatively, as described in Reaction Scheme 2, a 4-(3-$C_{1-3}$ straight-chain alkylamino)propyl-3-cyclohexen-1-one (III) can be treated with base in a mutual inert polar solvent, conveniently sodium methylate in methanol, to give the aforementioned cis-(±)-1-$C_{1-3}$ straight chain alkyl-7-oxodecahydroquinoline (IV). With prolonged treatment of the latter under the same basic conditions, the cis-(±)ketone is isomerized to the corresponding trans-(±)-1-$C_{1-3}$ straight-chain alkyl-7-oxodecahydroquinoline (V).

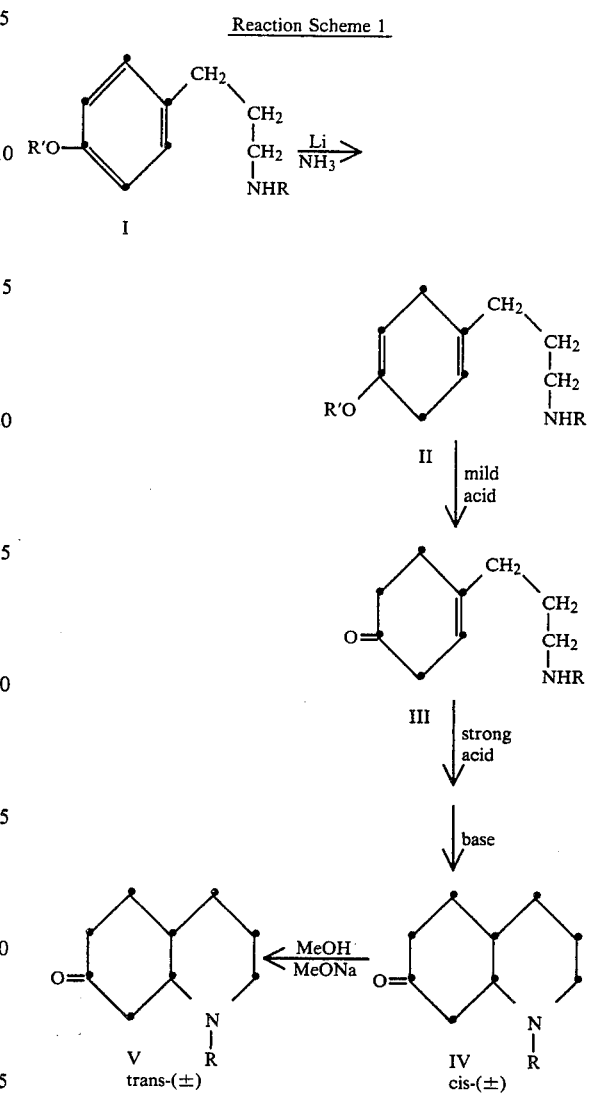

wherein R and R' are individually $C_{1-3}$ straight chain alkyl (methyl, ethyl or n-propyl).

Resolution either of the trans-(±) racemate or of the cis-(±) racemate followed by basic isomerization yields a 4aR,8aR-1-$C_{1-3}$ straight chain alkyl-7-oxodecahydroquinoline or a 4aS,8aS-1-$C_{1-3}$ straight chain alkyl-7-oxodecahydroquinoline.

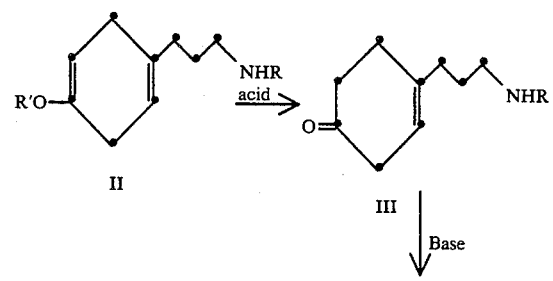

-continued
Reaction Scheme 2

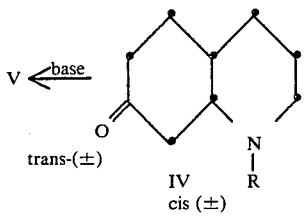

wherein R and R' have their previous significance.

One preparation of the starting material I is outlined below in Reaction Scheme 3. According to this procedure, a 3-(4-alkoxyphenyl)propionic acid (VI) is transformed to the acid chloride (VII) which, in turn, forms an amide (VIII) on reaction with a $C_{1-3}$ straight chain alkylamine. Alternatively, the amide (VIII) may be prepared by converting a p-(lower alkoxy) cinnamic acid to the corresponding N-$C_{1-3}$ straight-chain alkyl amide and then subjecting said amide to catalytic (noble metal catalyst) hydrogenation. Reduction of the amide with $LiAlH_4$ or $BH_3$ gives the desired starting material (I).

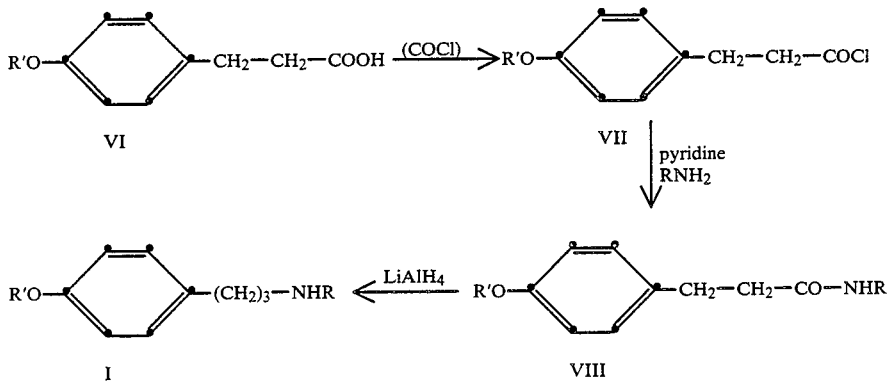

Reaction Scheme 3 wherein R and R' have their previous meanings.

Trans-($\pm$)-1-$C_{1-3}$ straight chain alkyl-7-oxodecahydroquinoline or one of its enantiomers is used to prepare the dopamine D-2 agonists, the trans ($\pm$)-5-$C_{1-3}$ straight chain alkyl-4,4a,5,6,7,8,8a,9-octahydro-oxazolo[4,3-g]quinolines via a Japp-Klingemann Reaction carried out on a 6-formyl derivative followed by hydrogenolysis of the phenylhydrazine product of that reaction. The 6-amino derivative thus prepared undergoes cyclization to a 5-substituted-4,4a,5,6,7,8,8a,9-octahydro-oxazolo[4,5-g]quinoline in the presence of formic acid, as set forth in the copending application of Schaus and Titus, Ser. No. 637,232, filed this even date.

SPECIFIC EMBODIMENTS OF THE INVENTION

The following specific embodiments of this invention illustrate its nature. The reaction conditions, solvents, reagents, etc., are, except where noted, exemplary only and should not be construed to limit in any way the invention to those specific disclosures.

EXAMPLE 1

A solution was prepared by dissolving 9.9 g of lithium in 2 l of anhydrous liquid ammonia. 98.7 g of 4-(3-n-propylamine)propylanisole were dissolved in a mixture of 27.8 ml of anhydrous ethanol and 300 ml of THF. This solution was added slowly in dropwise fashion with stirring to the lithium in liquid ammonia solution. After the addition had been completed, the reaction mixture was stirred for about 45 minutes. Water was then added slowly until the blue color of dissolved Li had been discharged. A stream of warm $N_2$ was passed over the reaction mixture overnight to evaporate the ammonia. Additional water was then added to dissolve the salts which had formed. The alkaline aqueous solution was extracted three times with equal volumes of diethyl ether. The ethereal extracts were combined and dried. Evaporation of the ether yielded 93.2 g of solvated 1-methoxy-4-(3-n-propylamino)propyl-1,4-cyclohexadiene; yield=93.5%.

One hundred twenty-one grams of 1-methoxy-4-(3-n-propylamino)propyl-1,4-cyclohexadiene were dissolved in 1 l of 15% aqueous sulfuric acid. The acidic solution was refluxed for about 6 hours and was then poured over ice. The dilute acidic solution was made basic with 50% aqueous sodium hydroxide. The now-basic aqueous solution was extracted with methylene dichloride. The methylene dichloride extract was dried and the solvent removed therefrom to yield 25.6 g of cis-($\pm$)-1-n-propyl-7-oxodecahydroquinoline.

About 23.8 g of the above product were dissolved without further purification in 300 ml of methanol to which solution was added 1.3 g of sodium methylate. The reaction mixture was stirred overnight at room temperature, and was then diluted with water. The aqueous mixture was made strongly basic and the basic mixture extracted with methylene dichloride. The methylene dichloride extract was dried, and the solvent removed therefrom to yield 11.4 g of trans-($\pm$)-1-n-propyl-7-oxodecahydroquinoline, plus 4.3 g of a mixture of the cis-($\pm$) and trans-($\pm$)isomers.

The compound had the following physical characteristics:

$IR(CHCl_3)$ 2904, 1457, 1081 $cm^{-1}$.

Proton NMR ($CDCl_3$, 270 MHz, $\delta$): 2.94 (bd, 1H, J=2.0; 2.79 (bd, 1H, J=2.5); 2.61–2.50 (m, 1H); 2.42–1.98 (m, 6H); 1.92–1.22 (m, 8H); 1.10–0.98 (m, 1H); 0.82 (t, 3H, J=1.2).

EXAMPLE 2

One-tenth gram of 4-(3-n-propylamino)propyl-1-methoxy-1,4-cyclohexadiene was stirred for 1 hour at room temperature in 15 ml of 0.1N hydrochloric acid. The reaction mixture was made basic with ammonium hydroxide. The basic aqueous mixture was extracted several times with equal volumes of $CH_2Cl_2$. The organic extracts were combined and dried. Evaporation of the solvent yielded a product which consisted of $\Delta^3$-4-(3-n-propylamino)propylcyclohexenone.

A repeat run with 5 g of cyclohexadiene starting material yielded a residue which, without further purification, was added to a solution of 14.9 millimoles of sodium methylate in 10 ml of methanol. The resulting solution was stirred at ambient temperatures for 18 hours, and was then poured into water. The alkaline layer was extracted several times with equal volumes of $CH_2Cl_2$. The organic extracts were combined and dried, and the solvent removed by evaporation in vacuo to give 4.5 g of a dark red-orange residue. The residue was dissolved in hexane/THF (2:1) containing a trace of $NH_4OH$, and the solution chromatographed over silica, using the same solvent as eluant. Early fractions yielded primarily cis-($\pm$)-1-n-propyl-7-oxodecahydroquinoline. Later fractions were shown to contain trans-($\pm$)-1-n-propyl-7-oxodecahydroquinoline; yield=2.34 g.

Preparation of Starting Material 4-(3-n-Propylamino)propylanisole was prepared according to the following series of reactions.

One hundred grams of 3-(p-anisyl)propionic acid were suspended in 200 ml of toluene. 48.5 ml (70.5 g) of oxalyl chloride were added thereto. Two drops of DMF were added, and the reaction mixture stirred at ambient temperature until homogenous by which time gas evolution had nearly ceased—about 2.5 hours, thus forming the corresponding acid chloride. The acid chloride solution was added in dropwise fashion to a solution of 41.9 ml (36.1 g) of n-propylamine and 67.4 ml (65.9 g) of pyridine in 600 ml of methylene dichloride at about $-10°$ C. After the addition had been completed, the cooling bath was removed. The mixture was stirred at room temperature for about 45 minutes and was then poured into water. The organic layer was separated, and the separated layer washed successively with equal volumes of 1% hydrochloric acid and 1% aqueous sodium bicarbonate and was then dried. Evaporation of the solvent yielded a solid which, on recrystallization from diethyl ether, yielded 91.9 g of N-n-propyl-(p-anisyl)propionamide.

Alternatively, 100 g of p-methoxy-cinnamic acid was suspended in 400 ml of toluene. About 25 ml of oxalyl chloride were added and the reaction mixture stirred at room temperature until gas evolution had ceased. Another 25 ml of oxalyl chloride were added and this reaction mixture stirred at room temperature overnight. The resulting nearly homogeneous reaction mixture containing p-methoxy-cinnamoylchloride formed in the above reaction, was added slowly to a solution of 50.8 g of n-propylamine, and 68.1 g of pyridine in 600 ml of methylene dichloride at about $-10°$ C. After the addition had been completed, the reaction mixture was allowed to warm to room temperature at which temperature it was stirred for about 9 hrs. The reaction mixture was poured into water. The organic layer was separated and washed successively with 1% hydrochloric acid and 1% sodium bicarbonate. The organic layer was dried. Evaporation of the solvent gave a solid, comprising N-n-propyl p-methoxycinnamoylamide formed in the above reaction. Recrystallizaton from MeOH/$Et_2O$ gave 112 g of product, which, without further purification, was hydrogenated at 60 psi in 875 ml of anhydrous ethanol over 13 g of a 5% Pd/C catalyst to yield 110 g N-n-propyl 3(p-anisyl)propionamide.

Next, about 31.3 g of $LiAlH_4$ and 500 ml of THF were placed in a 3 l R.B. flask equipped with stirrer and condenser. A solution of 91.1 g of N-n-propyl 3-(p-anisyl)propionylamide provided by either procedure in 700 ml of THF was added thereto. After the addition had been completed, the reaction mixture was heated to reflux temperature for about 3.5 hours and then stirred overnight at room temperature. 31 ml of water, 31 ml of 15% aqueous sodium hydroxide and 93 ml of water were added seriatim with caution while stirring was continued. The reaction mixture was filtered. Evaporation of the filtrate to dryness gave 83.2 g (97.5%) of a light yellow oil comprising 4-(3-n-propylamino)-propylanisole formed in the above reaction.

We claim:
1. The process which comprises
(a) reducing with lithium in liquid ammonia a compound of the formula

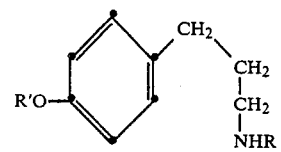

to yield a cyclohexadiene of the formula

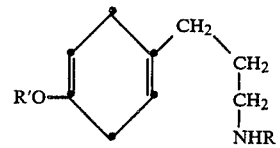

(b) hydrolyzing the enol ether and cyclizing the resulting cyclohexen-1-one to yield a cis-($\pm$)-1-$C_{1-3}$ straight chain alkyl-7-oxodecahydroquinoline of the formulas

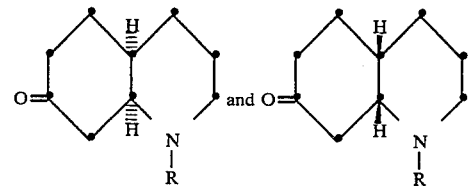

(c) and then isomerizing said cis-($\pm$) product with base in a mutual, non-reacting polar solvent to yield a trans-($\pm$)-1-$C_{1-3}$ straight chain alkyl-7-oxodecahydroquinoline of the formula

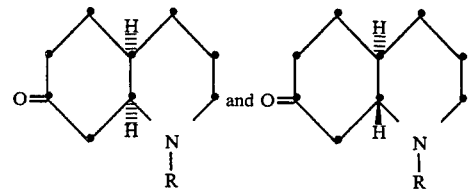

wherein R and R' are independently $C_{1-3}$ straight chain alkyl.

2. A process according to claim 1 in which R is n-propyl.
3. A cis± or trans± compound of the formula
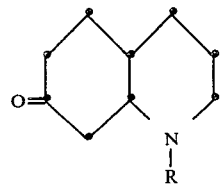
wherein R is $C_{1-3}$ straight chain alkyl.
4. A compound according to claim 3 in which R is n-propyl.
5. A cis-(±) racemate according to claim 3.
6. A trans-(±) racemate according to claim 3.
* * * * *

UNITED STATES PATENT AND TRADEMARK OFFICE
CERTIFICATE OF CORRECTION

PATENT NO. : 4,600,777
DATED : July 15, 1986
INVENTOR(S) : Diane L. Huser et al.

It is certified that error appears in the above—identified patent and that said Letters Patent is hereby corrected as shown below:

Column 6, lines 57-65, the formula which reads

" 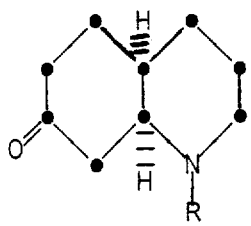 and 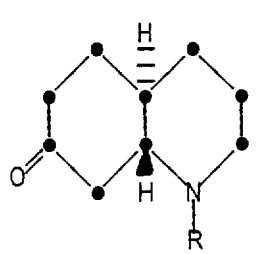 "

should read

-- 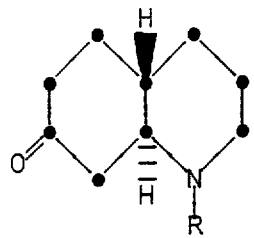 and 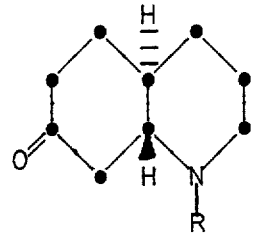 --

Signed and Sealed this

Fourteenth Day of April, 1987

Attest:

DONALD J. QUIGG

Attesting Officer    Commissioner of Patents and Trademarks